United States Patent [19]

Sittenthaler et al.

[11] Patent Number: 4,532,136
[45] Date of Patent: Jul. 30, 1985

[54] 4,4,4-TRICHLORO-1-PYRIDYL-BUT-2-ENE-1-ONES AND FUNGICIDES MADE THEREWITH

[75] Inventors: Wilhelm Sittenthaler, Munich, Fed. Rep. of Germany; Fritz Sauter, Vienna, Peter Stanetty, Harmannsdorf, both of Austria

[73] Assignee: Consortium Für Elektrochemische Industriegesellschaft GmbH, Munich, Fed. Rep. of Germany

[21] Appl. No.: 570,225

[22] Filed: Jan. 12, 1984

[30] Foreign Application Priority Data

Feb. 10, 1983 [DE] Fed. Rep. of Germany ....... 3304572
Oct. 24, 1983 [EP] European Pat. Off. ........ 83110602.6

[51] Int. Cl.$^3$ .................. C07D 213/50; A01N 43/40
[52] U.S. Cl. .................. 514/277; 546/314; 546/315
[58] Field of Search .............. 546/314, 315; 424/266

[56] References Cited

PUBLICATIONS

Kiehlmann, et al., "Synthesis and novel rearrangement of 1,1,1-trichloro 2-alken-4-ones", Chemical Abstracts 75:151316g.

Primary Examiner—Henry R. Jiles
Assistant Examiner—Dale A. Bjorkman
Attorney, Agent, or Firm—Collard, Roe & Galgano

[57] ABSTRACT

4,4,4-trichloro-(x-pyridyl)-but-2-ene-1-one, wherein x is 2, 3 and 4, and a process for making the same. The compounds are effective fungicides used singly or in combination.

2 Claims, No Drawings

4,4,4-TRICHLORO-1-PYRIDYL-BUT-2-ENE-1-ONES AND FUNGICIDES MADE THEREWITH

The present invention relates to 4,4,4-trichloro-1-pyridyl-but-2-ene-1-ones, their preparation and fungicides made therewith. Particularly, the invention relates to 4,4,4-trichloro-1-(2-pyridyl)-but-2-ene-1-one, 4,4,4-trichloro-1-(3-pyridyl)-but-2-ene-1-one and 4,4,4-trichloro-1-(4-pyridyl)-but-2-ene-1one. The novel compounds are effective fungicides. The compounds according to the invention are represented by the following formula

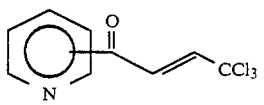

wherein the trichlorobutenoyl group may be situated in the 2-, 3-, or 4-position of the pyridine ring. The compounds may be prepared by dehydration of the corresponding 4,4,4-trichloro-3-hydroxy-1-pyridyl-butane-1-ones.

A preferred method of preparing the compounds of the invention is the dehydration of 4,4,4-trichloro-3-hydroxy-1-(x-pyridyl)-butane-1-one, wherein x means 2, 3 or 4, the dehydration taking place in the presence of sulfuric acid.

Preferably sulfuric acid of 50 to 100% by weight is used, advantageously sulfuric acid of 90 to 96% by weight. The proper amount of the sulfuric acid used will give a solution of the above mentioned starting materials in the acid. Usually, the solutions obtained are 20 to 30% by weight solutions in sulfuric acid.

The reaction temperature is preferably 10° to 50° C., especially 15° to 30° C.

As a rule, the procedure comprises the addition of the starting products to the sulfuric acid and stirring therein. The end of the reaction can be determined, e.g., by thin layer chromatography. Then, dilution with water is carried out, whereupon neutralization with bases takes place, and finally the end product is extracted with a polar solvent immiscible with water. Examples of such solvents are diethyl ether, ethyl acetate, methylene chloride, chloroform, and others.

The starting compounds 4,4,4-trichloro-3-hydroxy-1-pyridyl-butane-1-ones are available by addition of the corresponding acetylpyridines (2-acetylpyridine, 3-acetylpyridine or 4-acetylpyridine) to trichloroacetaldehyde in the presence of Lewis acids per mole acetylpyridine, 1-1.2 moles trichloroacetaldehyde and 1-1.2 moles of Lewis acid are used.

Examples of Lewis acids are $ZnCl_2$, $BF_3$, $AlCl_3$, $AlBr_3$ and others.

As a rule, the above mentioned addition reactions are carried out without solvent at temperatures from 70° to 110° C. If necessary the operations may be carried out in the presence of solvents, e.g., diethyl ether, dioxane, tetrahydrofuran, and others.

Alternatively, the synthesis of the above-mentioned starting compounds can be achieved by addition reaction of the acetylpyridines with trichloroacetaldehyde in the presence of bases, e.g., 1,4-diazabicyclo[2,2,2]octane or 1,5-diazabicyclo[5,4,0]undec-7-ene.

Per mole acetylpyridine, advantageously 1-1.2 moles of trichloroacetaldehyde and 0.1-0.5 moles, especially about 0.2 moles, of a base are added.

Suitable solvents are, as mentioned above, polar organic solvents, e.g., diethyl ether, dioxane, tetrahydrofuran and the like. The reaction temperatures are in the range of 50°-100° C. The isolation of the desired product is carried out by evaporation of the solvent, and recrystallization in alcohols, such as methanol, ethanol, or their mixtures with water.

The acetylpyridines used as basic chemicals, and trichloroacetaldehyde are commercially available products. It is desirable to use the aldehyde in freshly distilled condition.

The compounds made according to the invention are effective fungicides. They are used on plants affected by fungi or on plant products. Their use results in a curative effect.

They are effective, for instance, against cinerea, and fungi occurring together with the same, such as *Alternaria solani* and *Penicillium glaucum*. Further examples for their effectiveness are *Septoria nodorum, Verticillium dahliae, Fusarium culmorum, Fusarium nivale, Colletotrichum coffeanum* and others.

The products according to the invention are useful in many sectors of horticulture, without being limited thereto. Examples are viniculture, house gardens, lettuce plantings, ornamental plants, e.g., alpine violets, geraniums, in the cultivation of rape, of strawberries, stone fruits, and agriculture.

The products of the invention can be used alone or in mixture with other pesticides, especially other fungicides. In general, they are used mixed with solid or liquid diluents, or in solutions with solid or liquid solvents, the contents of the inventive products being 0.01-95% by weight.

As a rule, the mixtures or solutions are used in the form of emulsion concentrates, suspension concentrates, pastes, spraying powders, dusting agents, granulates or microcapsules.

Emulsion concentrates and pastes contain usually 10-60% by weight, preferably 15-40% by weight, of effective agent, 2-5% auxiliary dispersing agents, organic solvents and/or water.

Spraying powders contain mostly 10-80% by weight, preferably 15-70% by weight, of effective agent, 1-10% auxiliary dispersing agents and 10-89% by weight of inert components.

Granulates and dusting agents contain in addition to inert components binding agents and/or coating agents 1-10% by weight, preferably 5-10% by weight, of effective agent.

According to the invention, the following substances are used:
  As auxiliary dispersing agents, e.g., alkyl- and aryl sulfonates, methyl cellulose, polymer sulfonic acids and their salts, polyalcohols, fatty acid esters, fatty alcohol ethers, fatty amines;
  As organic solvents, e.g., alcohols, e.g., ethanol, butanols, dimethylformamide, dimethylsulfoxide, N-methyl-pyrrolidone, aromatics, e.g., toluene and xylenes;
  As inert components, e.g., kaolin, china-clay, talcum, calcium carbonate, highly dispersed silicic acid, silica gels, kieselgur, diatomaceous earth, pumice, crushed corn, thickening agents, e.g., starch and carboxymethyl cellulose;

As binding agents, e.g., magnesium sulfate, gypsum and gum arabic;

Used are, for instance, the following combinations:

1. Emulsion Concentrate:
   50% by weight effective agent
   42% by weight N-methyl-pyrrolidone
   8% by weight nonylphenolpolyglycol ether
2. Spraying Powder:
   50% by weight effective agent
   41.5% by weight silica trade name "Silitin")
   2% by weight sodium ligninsulfonate
   5% by weight alkylpolyglycol ether
   1.5% by weight polypropyleneglycol
3. Suspension concentrate:
   50% by weight effective agent
   5% by weight ethylene glycol
   1.5% by weight highly dispersed silicic acid ("HDK")
   0.5% by weight defoaming agent
   5% by weight octylphenolpolyglycol ether
   38% by weight water The amounts on effective agents may vary within wide limits.

The application of the effective agents may occur in any desired form. For instance, by casting, spraying, dusting, or coating.

In the following, the invention will be described by a number of examples, but it should be understood that these are given by way of illustration and not of limitation.

EXAMPLE 1

Preparation of 4,4,4-trichloro-1-(3-pyridyl)-but-2-ene-1-one.

(a) 3 g (0.025 moles of 3-acetylpyridine, 3.65 g (0.025 moles) of freshly distilled trichloroacetaldehyde, and 3.4 g (0.025 moles of anaqueous zinc chloride were heated for 2.5 hours to 90° C., while stirring. Thereafter, they were dissolved in a mixture of water/methylene chloride, the phases were separated, the organic phase was dried, and finally the solvent was evaporated. The raw product obtained was recrystallized from methanol. Obtained were 4.2 g (corresponding to 63% of the theoretical) of 4,4,4-trichloro-3-hydroxy-1-(3-pyridyl)-butane-1-one having a melting point of 129°–131° C.

(b) 5 g (0.018 moles) of 4,4,4-trichloro-3-hydroxy-1-(3-pyridyl)-butane-1-one were stirred for 5 hours at 20° C. in 50 ml 96% by weight of sulfuric acid. Then dilution with 50 ml water and neutralization with saturated sodium bicarbonate solution took place. Thereupon, the solution was extracted with the same volume of diethyl ether. The organic phase was also washed with water, dried over sodium sulfate and finally evaporated. Obtained were 3.5 g (78% of the theoretical) of 4,4,4-trichloro-1-(3-pyridyl)-but-2-ene-1-one, having a melting point (with decomposition) of 133°–136° C.

EXAMPLE 2

Preparation of 4,4,4-trichloro-1-(2-pyridyl)-but-2-ene-1-one.

The procedure of Example 1 was repeated using 3 g (0.025 moles) of 2-acetylpyridine instead of 3-acetylpyridine.

In analogy to Example 1a, 4.0 g (60% of the theoretical) of 4,4,4-trichloro-3-hydroxyl-1-(2-pyridyl)-butane-1-one were obtained as an oily mass. The substance is characterized by the following NMR data:

$^1$H-NMR (acetone-d$_6$): $\delta = 8.75$ (m,1H); 8.1 (m,2H); 7.7–7.5 (m,1H); 6.0 (b,1H); 4.9 (dd,1H); 4.0–3.6 ppm (dd, 2H);

5 g (0.018 moles) of 4,4,4-trichloro-3-hydroxy-1-(2-pyridyl)-butane-1-one were treated with sulfuric acid in analogy to example 1b. Obtained were 2.2 g (50% of the theoretical) of 4,4,4,-trichloro-1-(2-pyridyl)-but-2-ene-1-one as an oily mass. The substance is characterized by the following NMR data:

$^1$H-NMR (acetone d$_6$): $\delta = 8.75$ (m,1H); 8.1 (m,2H); 7.75 (m,1H); 8.25–7.25 ppm AB system with $\delta_A = 8.15$ and $\delta_B = 7.35$ ppm and $J_{AB} = 15$ Hz.

EXAMPLE 3

Preparation of 4,4,4-trichloro-3-hydroxy-1-(4-pyridyl)-but-2-ene-1-one.

The procedure of Example 1 was repeated using 3 g (0.025 moles) of 4-acetylpyridine instead of 3-acetylpyridine.

In analogy to Example 1a, 2.7 g (40% of the theoretical of 4,4,4-trichloro-3-hydroxy-1-(4-pyridyl)-butane-1-one, melting point 175° C., were obtained.

5 g (0.018 moles) of this substance were treated with sulfuric acid as described in Example 1b. Obtained were 4.2 g (95% of the theoretical) of 4,4,4-trichloro-1-(4-pyridyl)-but-2-ene-1-one, in the form of brown crystals. Decomposition point 150° C.

Characterizing data:

$^1$H-NMR (DMSO-d$_6$): $\delta = 8.95$ (m,2H); 7.95 (m,2H); 7.7–7.25 ppm AB-system with $\delta_A = 7.55$ and $\delta_B = 7.39$ ppm and $J_{AB} = 15$ Hz In the following, the effective agents are designated by A, B and C as shown here.

4,4,4-trichloro-1-(2-pyridyl)-but-2-ene-1-one by A
4,4,4-trichloro-1-(3-pyridyl)-but-2-ene-1-one by B
4,4,4-trichloro-1-(4-pyridyl)-but-2-ene-1-one by C.

EXAMPLE 4

Germination Test of Spores

50 μl of a solution containing effective agents in the amounts shown in the Table below were mixed with 50 μl of a spore suspension, made by rinsing off the spores from an agar culture with a nutrient solution, which contained per liter 10 g of sugar, 1 g of glycol, 1 g of KH$_2$PO$_4$ and 0.5 g of magnesium sulfate.

The mixed substances were placed into the concavity of an object carrier. The carriers were stored for 48 hours at 20° C. in a Petri dish whose bottom was covered with a wetted filtering paper. Then, the ratio of the germinated and ungerminated spores was compared with an untreated control specimen.

The effectiveness was calculated in % as shown in the Table below:

$$100 - \frac{\text{Number of germinated spores, treated}}{\text{Number of germinated spores, untreated}} \times 100$$

In all cases, limiting concentrations in ppm of the active agents were determined, in which a minimum 80% effectiveness, i.e., an inhibition of germination of spores was obtained.

TABLE

Limiting concentration in ppm of active agent at 80% effectiveness in the spore germinating test.

|  | A | B | C |
|---|---|---|---|
| *Alternaria solani* | 250 | 62 | 250 |
| *Botrytis cinerea* | 125 | 62 | 125 |
| *Fusarium culmorum* | 125 | 31 | 125 |
| *Fusarium nivale* | 31 | 31 | 125 |
| *Verticillium dahliae* | 125 | 62 | 125 |
| *Penicillium glaucum* | 62 | 31 | 250 |
| *Colletotrichum coffeanum* | 62 | 62 | 125 |

EXAMPLE 5

Grape juice Test 20 ml of a nutrient solution consisting of grape juice and sterilized water in the ratio 1:1 were filled into glass Petri dishes and effective substance was added thereto. Subsequently, the mixture was inoculated with 50 μl of a suspension of Botrytis spores, obtained by rinsing off the Botrytis spores from an agar culture with distilled water. After a germination period of 20 days at 20° C., the amount of fungus development on the surface of the nutrient solution was evaluated.

The effectiveness in % was calculated by the formula:

$$100 - \frac{\text{fungus growth, treated}}{\text{fungus growth, untreated}} \times 100$$

Result:

The limiting concentration of a minimum 80% effectiveness against Botrytis cinerea in grape juice with the use of A at 31 ppm
B at 4 ppm
C at 31 ppm Although only a few examples of the present invention have been described, it is obvious that many changes and modifications may be made thereunto, without departing from the spirit and scope of the invention.

What is claimed is:

1. 4,4,4-trichloro-(x-pyridyl)-but-2-ene-1-one, wherein x is 2, 3 or 4.

2. A fungicidal composition comprising 0.01–95% by weight of 4,4,4-trichloro-(x-pyridyl)-but-2-ene-1-one, wherein x is 2, 3 or 4, as the active agent, and a carrier selected from the group consisting of a liquid, a solid and mixtures thereof.

* * * * *